United States Patent
Wack et al.

(10) Patent No.: US 7,716,003 B1
(45) Date of Patent: May 11, 2010

(54) MODEL-BASED MEASUREMENT OF SEMICONDUCTOR DEVICE FEATURES WITH FEED FORWARD USE OF DATA FOR DIMENSIONALITY REDUCTION

(75) Inventors: Daniel C. Wack, Los Altos, CA (US); Andrei Veldman, Issaquah, WA (US); Edward R. Ratner, Los Altos, CA (US); John Hench, Los Gatos, CA (US); Noah Bareket, Saratoga, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 171 days.

(21) Appl. No.: 11/879,227

(22) Filed: Jul. 16, 2007

(51) Int. Cl.
*G01R 27/28* (2006.01)

(52) U.S. Cl. .................. 702/117; 702/159; 702/172; 356/625

(58) Field of Classification Search .................. 702/58, 702/117, 118, 127, 155, 159, 170–172; 356/625, 356/369; 700/121
See application file for complete search history.

(56) References Cited

U.S. PATENT DOCUMENTS

| | | | | |
|---|---|---|---|---|
| 6,483,580 | B1 * | 11/2002 | Xu et al. | 356/300 |
| 6,577,389 | B2 | 6/2003 | Biellak et al. | |
| 6,614,520 | B1 | 9/2003 | Bareket et al. | |
| 6,931,618 | B1 | 8/2005 | Tabery et al. | |
| 6,967,349 | B2 * | 11/2005 | Bonifield et al. | 257/48 |
| 6,989,896 | B2 | 1/2006 | Wen et al. | |
| 7,069,153 | B2 | 6/2006 | Johnson | |
| 7,099,005 | B1 | 8/2006 | Fabrikant et al. | |
| 7,151,594 | B2 | 12/2006 | Den Boef et al. | |
| 2003/0028358 | A1 * | 2/2003 | Niu et al. | 703/2 |

* cited by examiner

*Primary Examiner*—Manuel L Barbee
(74) *Attorney, Agent, or Firm*—Okamoto & Benedicto LLP (57) ABSTRACT

The present application discloses a new technique which reduces the dimensionality of a feature model by re-use of data that has been obtained by a prior measurement. The data re-used from the prior measurement may range from parameters, such as geometrical dimensions, to more complex data that describe the electromagnetic scattering function of an underlying layer (for example, a local solution of the electric field properties).

14 Claims, 9 Drawing Sheets

MODEL-BASED MEASUREMENT OF SEMICONDUCTOR DEVICE FEATURES WITH FEED FORWARD USE OF DATA FOR DIMENSIONALITY REDUCTION

TECHNICAL FIELD

1. Background of the Invention

The present disclosure relates to apparatus and methods for inspecting and analyzing semiconductor wafers and other substrates using scatterometry and related techniques.

2. Description of the Background Art

Scatterometry refers to an optical technique that analyzes diffraction to deduce structural details of a diffracting sample. The diffracting sample is generally a periodic structure, that is, a grating. Scatterometry may be used to measure or analyze two-dimensional structures (line gratings), as well as three-dimensional structures (such as periodic patterns of mesas or vias on a substrate).

Metrology methods using scatterometry rely on being able to accurately model the features that are being measured, calculate the light diffraction properties of the feature, and find a match between the calculated and measured values. In other words, theoretical model is defined for each physical structure to be analyzed, and calculated data using the model is then compared or analyzed against measured data. Typically, the measured data are related to the light diffraction efficiency as a function of wavelength, incidence angle, or both.

As the complexity of features increase, so do the number of parameters needed to model the features. Complexity may arise from multiple layers of materials and shapes that form the feature (for example, a complex gate structure), or from underlying layers of features that affect the diffracted light.

The computational processing needed to perform the calculations scales strongly (nearly exponentially) with the number of parameters in the model. For example, if the number of parameters doubles, then the processing required typically increases by a factor much greater than two. In practice, as the number of parameters in the model increases, the measurement using scatterometry becomes substantially more difficult and/or time consuming.

A library mode for performing scatterometry refers to an approach that uses pre-computed libraries of predicted measurements. In this approach, parameters of the model are varied over ranges, and a solution is calculated for each variation so as to create a library of solutions. When an actual measurement is made, a best fit may be determined by searching the library. Unfortunately, using such a library mode, the number of pre-calculated solutions becomes prohibitively large as the number of parameters becomes large.

Alternatively, in a real-time regression mode of performing scatterometry, the processing time to a solution becomes prohibitively long as the number of parameters becomes large. Prior attempts to reduce the processing time include using parallel or distributed processing. However, that approach is costly and limited in that the increase in speed from the parallel or distributed processing may not be able to keep up with the increase in computational complexity as the number of parameters becomes larger.

Furthermore, in either library mode or real-time regression mode, correlation of parameters may disadvantageously limit the precision and accuracy of the scatterometry measurement. For example, there may be a correlation between the height and width of a feature in that changes in either height or width may result in similar diffraction spectra. A precise and accurate determination of one parameter (for example, feature width) is undesirably hindered due to such correlation with another parameter (for example, feature height).

It is desirable to improve inspection and metrology for the manufacture of semiconductors and other substrates. More particularly, it is desirable to improve the speed, precision and accuracy of scatterometry-based inspection and metrology.

SUMMARY

The present application discloses a new technique which reduces the dimensionality of a feature model by re-use of data that has been obtained by a prior measurement. The data re-used from the prior measurement may range from parameters, such as geometrical dimensions, to more complex data that describe the electromagnetic scattering function of an underlying layer (for example, a local solution of the electric field properties). Other embodiments, aspects, and features are also disclosed.

DETAILED DESCRIPTION

As described below, the present application discloses a new technique which reduces the dimensionality of a feature model by re-use of data that has been obtained by a prior measurement. The data re-used from the prior measurement may range from parameters, such as geometrical dimensions, to more complex data that describe the electromagnetic scattering function of an underlying layer (for example, a local solution of the electric field properties).

In accordance with an embodiment of the invention, there is a need for specific procedures to obtain the relevant data from the pertinent source, to forward the relevant data, and to use the forwarded data to reduce the dimensionality of the computation of a current scatterometry measurement. The elements of a system to implement this feed forwarding of data may include: a means to determine the optimal source of the prior data; a means to collect and process the prior data and to store it in a database when required; a means to retrieve the prior data from the database and forward it to the real-time measurement algorithm; and a means to incorporate the prior data in the measurement algorithm.

The prior measurement and data derived therefrom may come after a prior process step of the same wafer (see description below in relation to FIGS. 2A, 2B, 2C, 3A, 3B, and 3C), or, alternatively, from a specially designed test feature that is adjacent to, or in the vicinity of, the feature of interest (see description below in relation to FIGS. 4 and 5).

In the mode where the optimal source of the prior data includes a measurement of underlying layer(s) during a prior process step, the underlying layer(s) may be measured by scatterometry, or by other techniques, including atomic force microscopy, critical dimension scanning electron microscopy (CD-SEM), or overlay measurements. Each of these techniques produces data which may be used to reduce the complexity of the scatterometry feature model. For complex features, this process may be extended to include more than one prior measurement. Once the prior measurement data is collected, it is preferably stored in a database that associates each data set with a specific wafer and a specific site on the wafer. Such databases may be configured either on the measurement tool computer or on a remote server. During the measurement process, the measurement tool uses a means to identify an appropriate data set that is associated with the target of interest and forward that data set to the measurement algorithm.

Alternatively, if the process flow in the fabrication facility does not lend itself to acquiring the data in a prior process step, the data may be obtained from a special test target on the wafer. Preferably, the test target is adjacent to the feature of interest. For example, the test target may be designed and fabricated to include all the features of the underlying layers, while not including features of the current layer. In this case, the measurement may proceed in two steps. In a first step, one or more features are measured from the reference test target. In a second step, a measurement is made on the target of interest, where measurement data from the first step is used in the second step to reduce the computational complexity of the second step. For complex features, this process may be extended to include more than one test target.

The method disclosed herein synergistically extends the practicality of model-based scatterometry measurements to complex features which were previously impractical to measure due to speed and/or correlation problems. Several heretofore unrealized advantages are gained by using the method disclosed herein. First, the speed of the model-based measurement is greatly increased. Second, undesirable parameter correlation is reduced, thus increasing the measurement precision and accuracy. The parameter correlation is reduced between those parameters which were previously determined (for example, a parameters of an underlying layer) and those parameters which are currently being determined (for example, shape parameters of a top layer).

Figure 1:
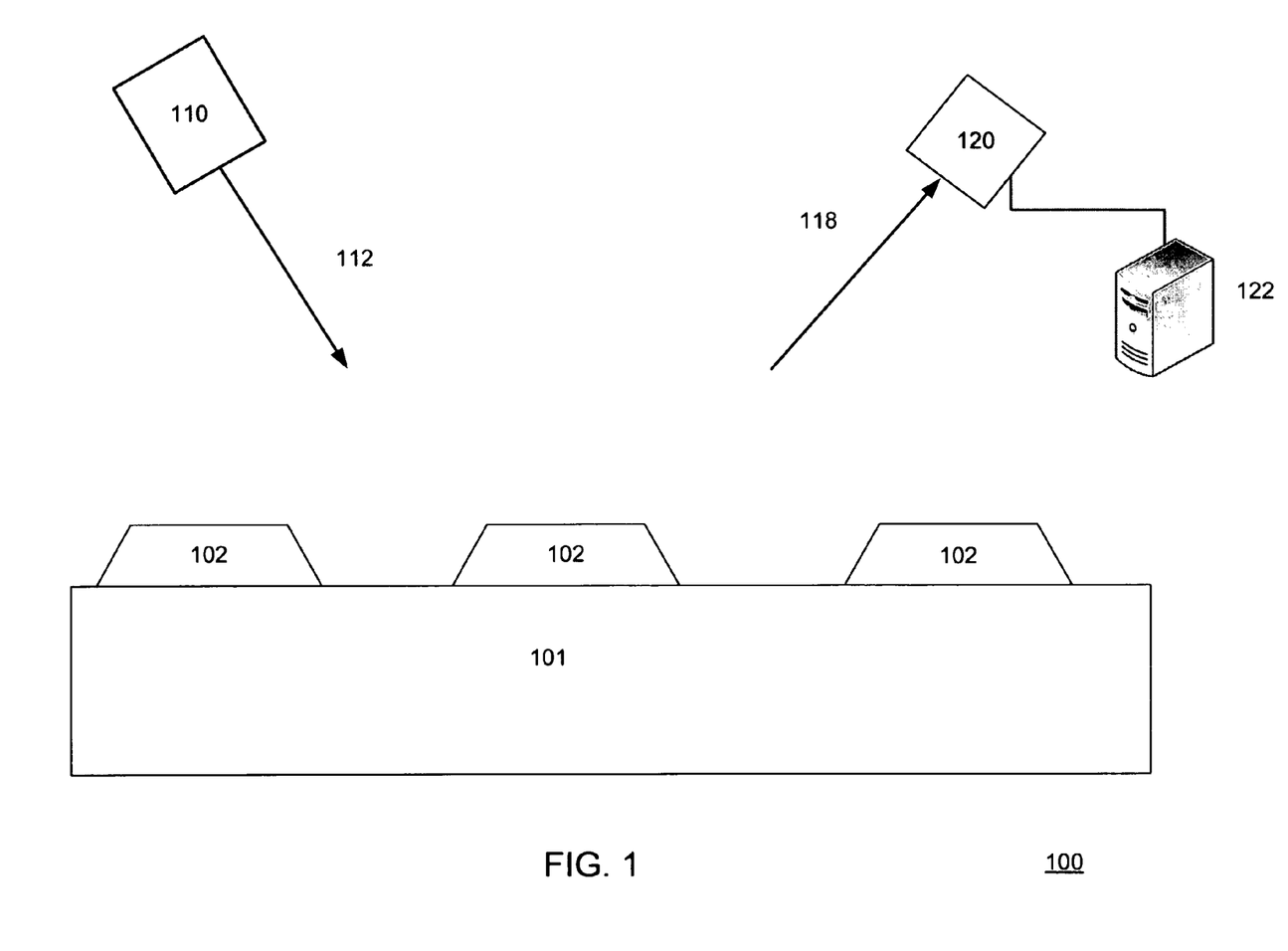
FIG. 1 is a schematic diagram depicting a scatterometry configuration applied to a semiconductor wafer with devices formed thereon in accordance with an embodiment of the invention.

FIG. 1 is a schematic diagram depicting a scatterometry configuration 100 applied to a semiconductor wafer with devices formed thereon in accordance with an embodiment of the invention. More particularly, FIG. 1 shows an example target substrate 101 upon which have been fabricated an array of features, in this case mesas 102 on the surface of the substrate.

As shown in FIG. 1, a typical scatterometry configuration includes an illumination source 110 that produces a monochromatic or polychromatic light beam 112. The light beam may be focused by an illumination lens system (not illustrated) to illuminate a spot or region on the surface of a target substrate 101. The light is diffracted or scattered by features in the illuminated region. The diffracted or scattered light 118 is focused by a collection lens system (not illustrated) to a detector 120.

The detection of the diffracted light provides diffraction data which may then be processed by a data processing system 122. The data processing system 122 may include various components, such as a processor for executing computer-readable instructions, a data storage system for storing the computer-readable instructions and other data, memory for holding the computer-readable instructions and other data, input and output interfaces, and a bus or other communications system which interconnects the components.

In accordance with an embodiment of the invention, the data processing system is configured to perform computations and other processing steps used to make measurements using scatterometry. In accordance with an embodiment of the invention, the data processing system is further configured to implement a database system which may be used to store and retrieve dimension data and other property data associated with particular measurement locations for specific identified wafers.

Further details regarding an example scatterometer system is given, for example, in U.S. Pat. No. 6,483,580, "Spectroscopic Scatterometer System," Yiping Xu and Ibrahim Abdulhalim, assignee KLA-Tencor Technologies Corporation. The disclosure of U.S. Pat. No. 6,483,580 is hereby incorporated by reference.

Figure 2A:
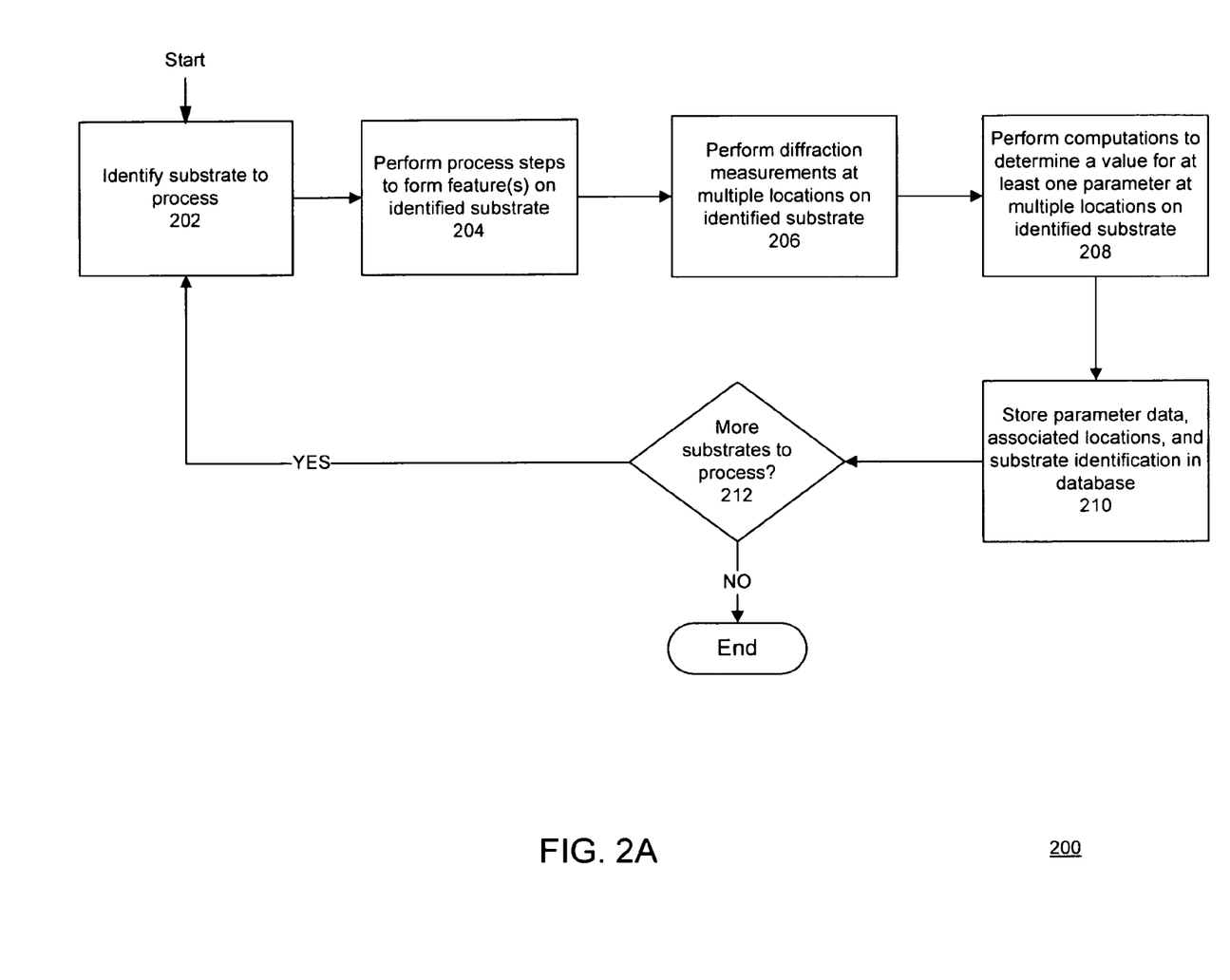
FIGS. 2A, 2B and 2C are flow charts depicting a method of model-based measurement of semiconductor device features with feed forward use of data for dimensionality reduction in accordance with an embodiment of the invention.
Figure 2B:
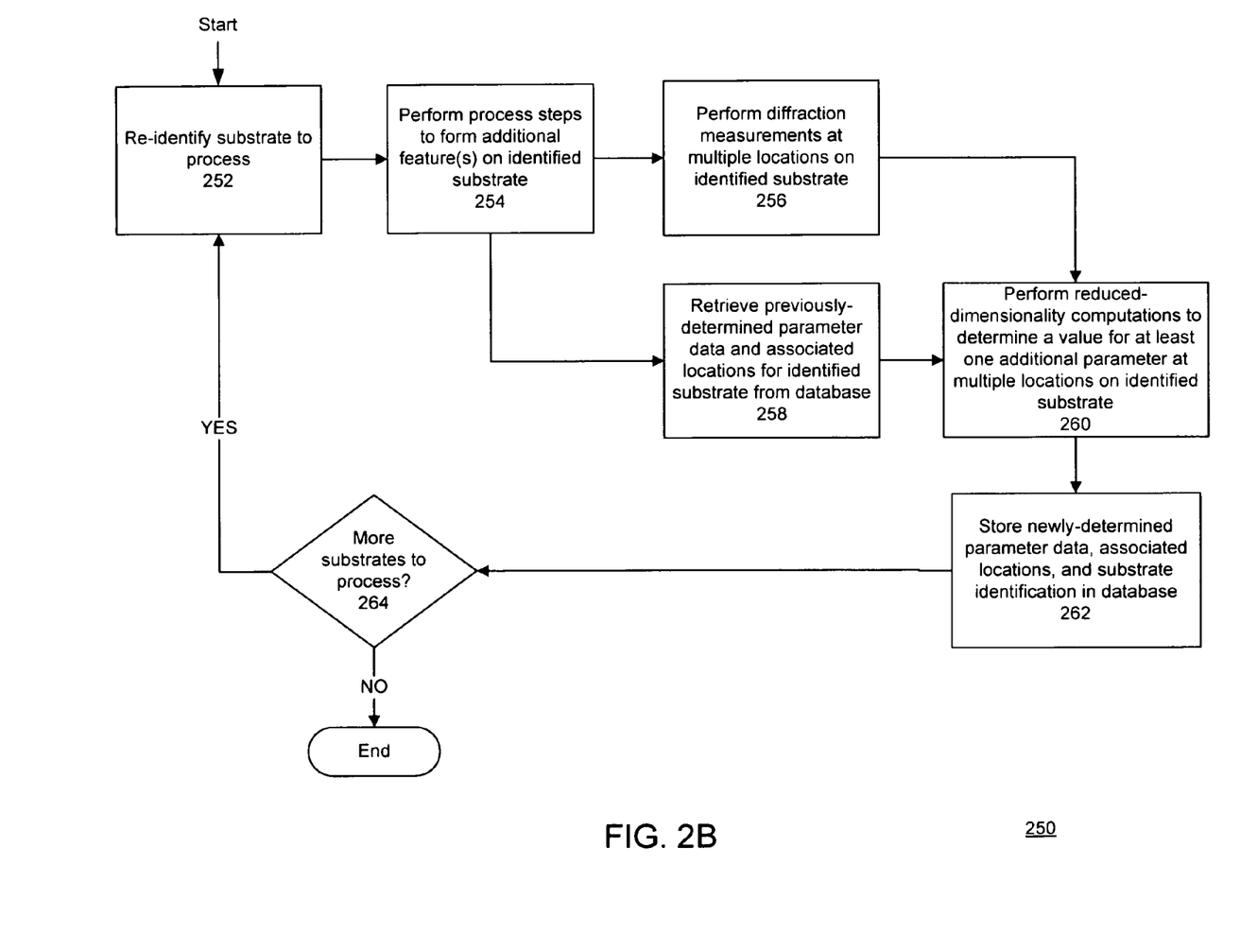
Figure 2C:
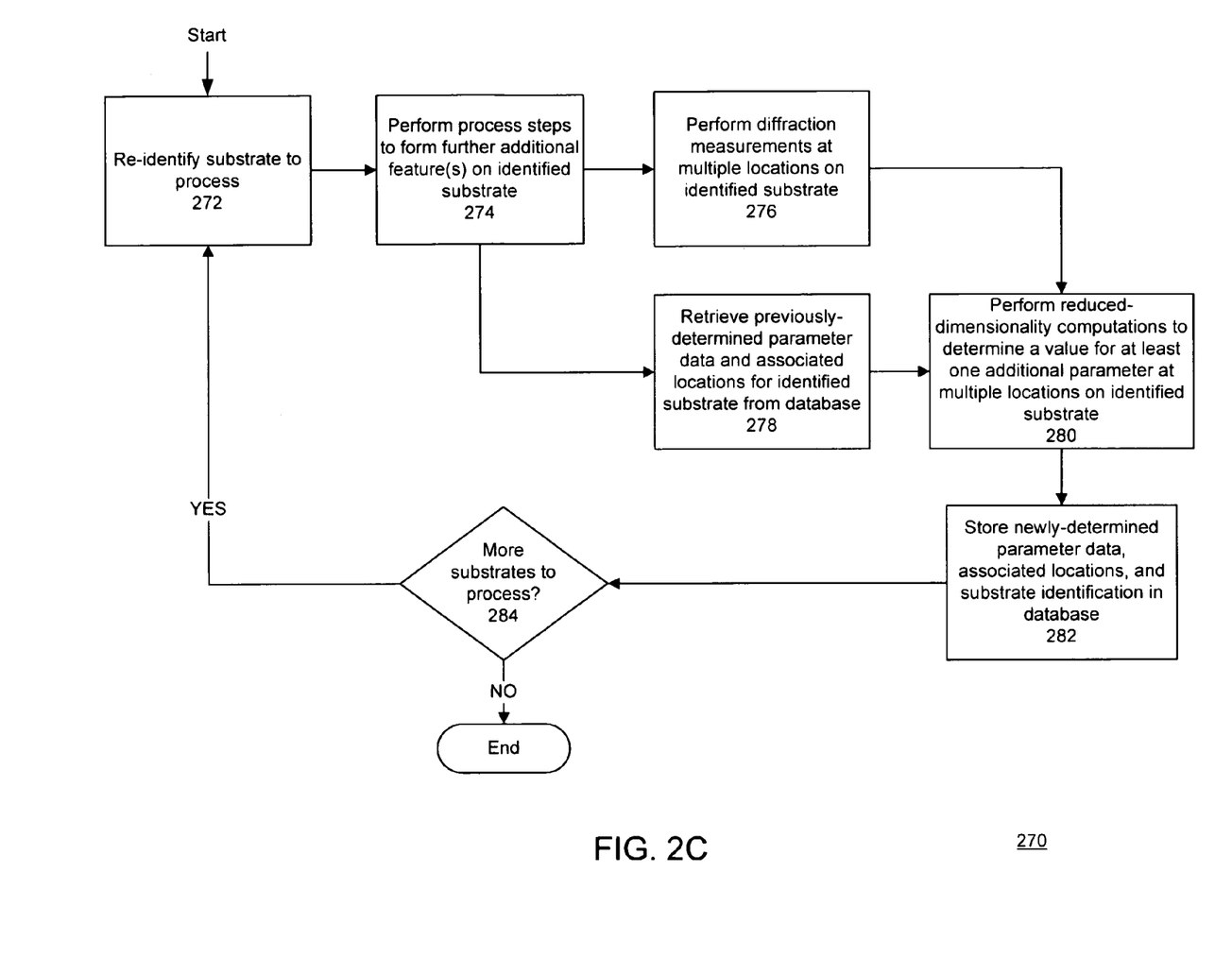
Figure 3A:
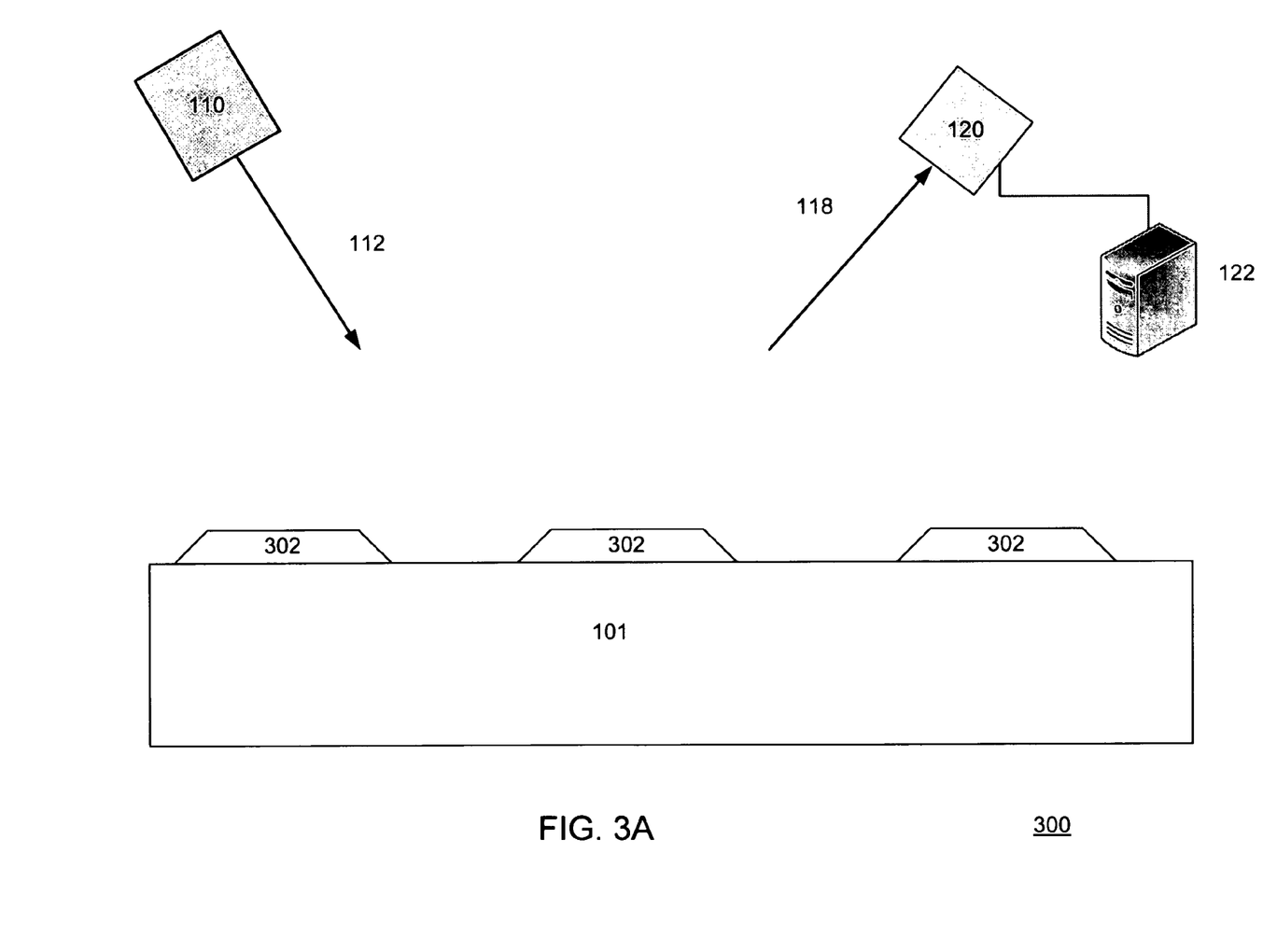
FIGS. 3A, 3B, and 3C are schematic diagrams depicting a scatterometry configuration applied at various points during processing of a semiconductor wafer in accordance with an embodiment of the invention.
Figure 3B:
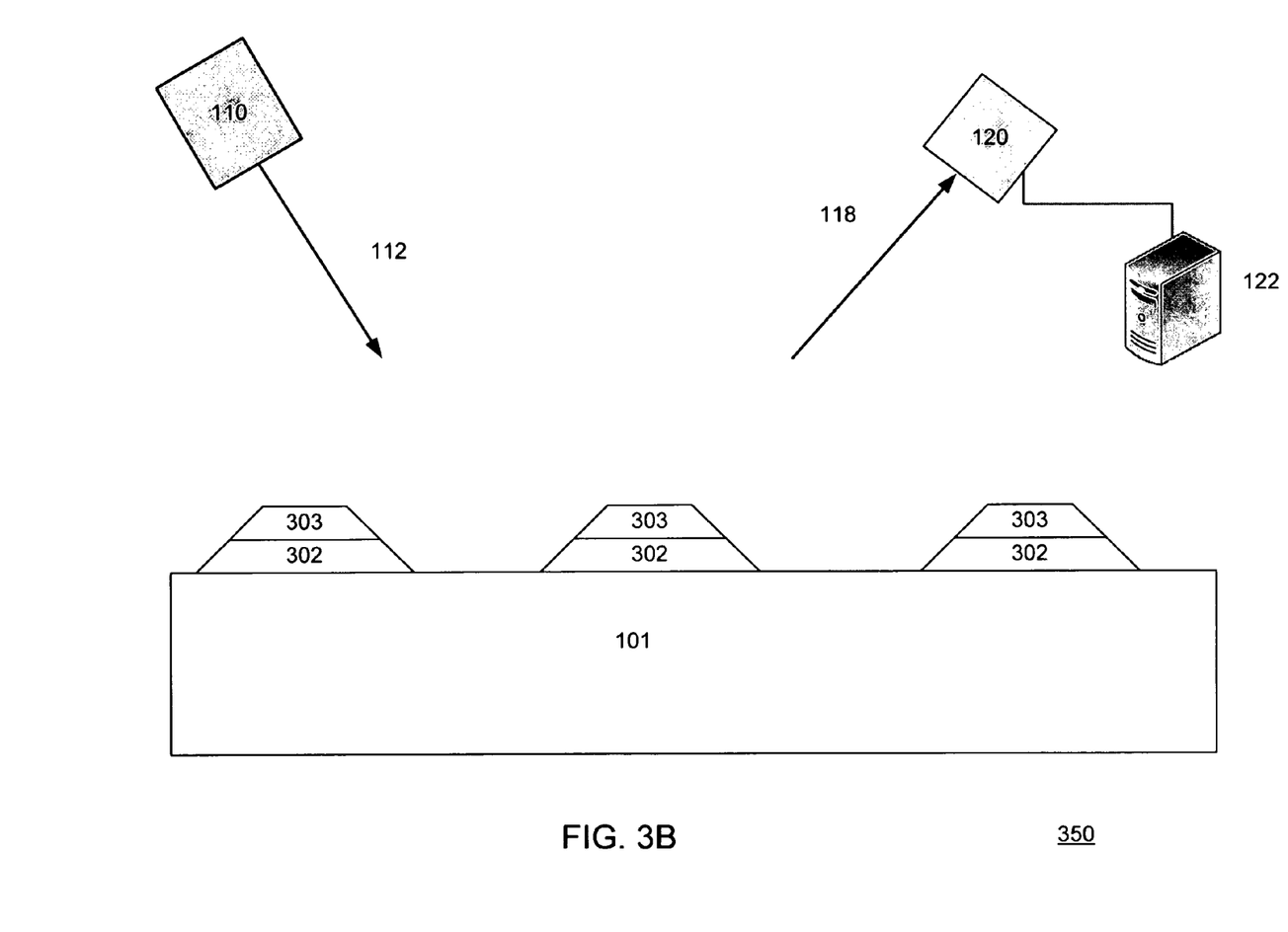
Figure 3C:
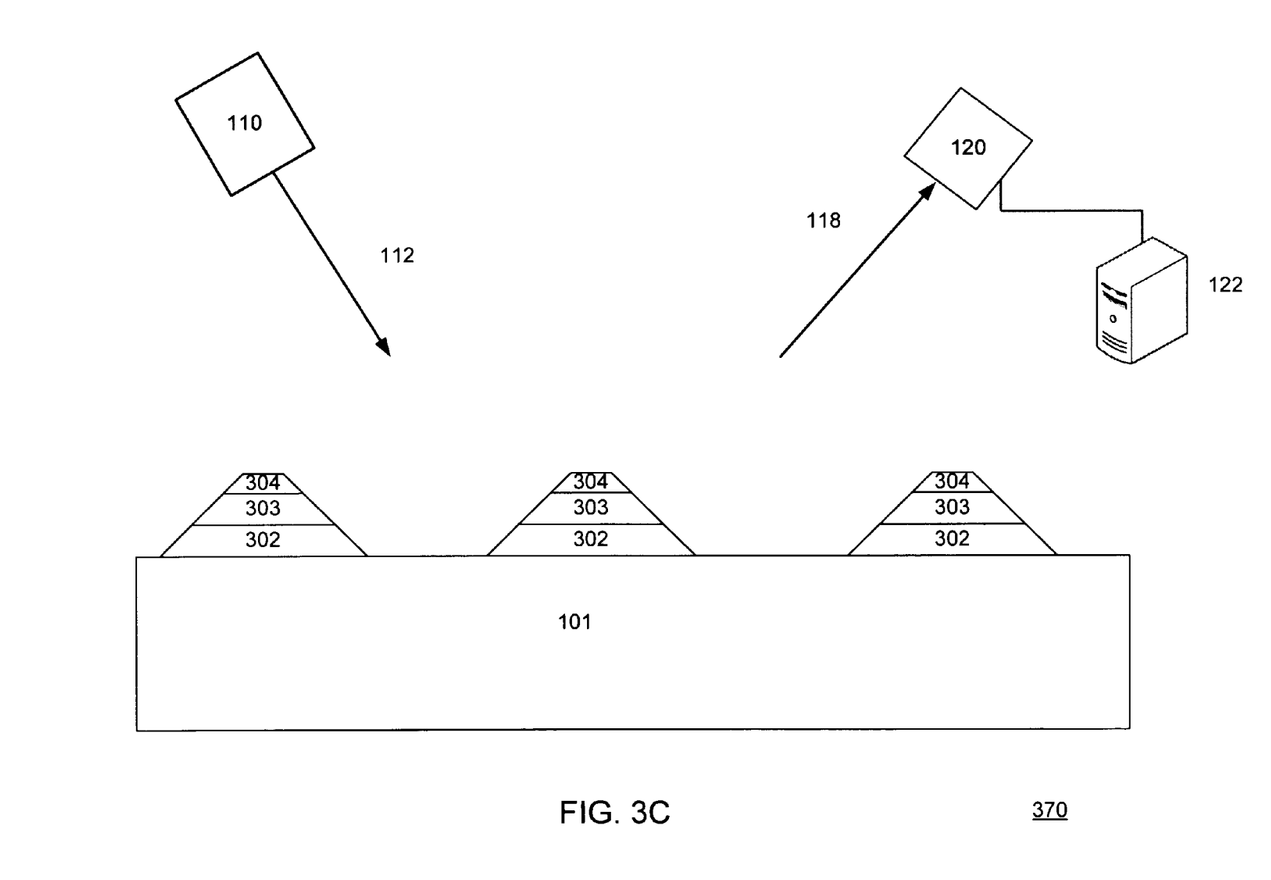

FIGS. 2A, 2B and 2C are flow charts depicting a method 200 of model-based measurement of semiconductor device features with feed forward use of data for dimensionality reduction in accordance with an embodiment of the invention. FIG. 2A relates to forming a first feature (or a first set of features) and making measurements and computations thereof. FIG. 2B relates to forming a second feature (or a second set of features) and making measurements and computations thereof. FIG. 2C relates to forming a third feature (or a third set of features) and making measurements and computations thereof.

The procedure 200 of FIG. 2A begins by identifying 202 the substrate to process. Such identification of a substrate may take the form, for example, of a wafer identification number which may be read by a bar code scanner system.

Processing steps are performed 204 to form a feature or features on the identified substrate. For example, consider the configuration 300 of FIG. 3A which shows a substrate 101 after processing steps have been performed to form a grating with a first layer 302 on the substrate surface.

Diffraction measurements may then be performed 206 at multiple locations on the identified substrate. The multiple locations may be predetermined sample locations on a wafer, for example. For example, consider FIG. 3A which shows a diffraction measurement being performed on the grating with the first layer 302 on the substrate surface.

Subsequently, computations are performed to determine 208 a value for at least one parameter (for example, physical dimensions and/or parameters relating to the electromagnetic scattering function) of the feature(s) at the multiple locations on the identified substrate. These computations are the aforementioned model-based computations and may comprise, for example, library mode or real-time regression mode computations.

The parameter data, associated locations, and the substrate identification are then stored 210 in a database. For example, the database may be implemented as part of the data processing system 122 in FIG. 3A. The database may later be accessed to rapidly retrieve the stored data.

A determination 212 may be made as to whether there are more substrates to process in accordance with FIG. 2A. In other words, the procedure of FIG. 2A may be used to process, and make measurements upon, various individual substrates being manufactured.

The procedure 250 of FIG. 2B also begins by re-identifying 252 the substrate to process. Such re-identification is typically needed because the processing of wafers may occur, for example, in batches.

Processing steps are performed 254 to form a feature or features on the identified substrate. For example, consider the configuration 350 of FIG. 3B which shows a substrate 101 after processing steps have been performed to form a second layer 303 on top of the first layer 302 in the grating pattern.

Diffraction measurements may then be performed 256 at multiple locations on the identified substrate. Preferably, these multiple locations are the same ones as the multiple locations referred to in FIG. 2A.

In addition, according to an embodiment of the present invention, previously-determined parameter data, along with associated locations, are retrieved 258 for this identified substrate from the database. For example, with reference to FIG. 3A, the shape parameters (such as, width, length, wall angle, and layer thickness) of the grating comprising the first layer 302 (and perhaps also the thickness and scattering function parameters of the layer) at the multiple locations on the substrate may be retrieved from the database.

Subsequently, using the parameter data retrieved from the database, reduced-dimensionality computations may then be performed 260 to determine a value for at least one additional parameter at the multiple locations on the identified substrate. Advantageously, using the "feed forward" data from the previous processing step reduces the dimensionality (and, hence, reduces the complexity) of the scatterometry computation required for the current processing step. For example, with reference to FIG. 3B, the shape parameters of the grating comprising the first 302 and second 303 layers (and perhaps also the thickness and scattering function parameters of the layers) at the multiple locations on the substrate may be determined with less variable parameters and hence with substantially less complexity by using the previously-determined parameters relating to the first layer 302.

In accordance with an embodiment of the invention, the feed forward process may continue to further processing steps and scatterometry measurements. In such an embodiment, the parameter data and associated locations for the identified substrate, as determined in the preceding step 260, are then stored 262 in the database. For example, with reference to FIG. 3B, the shape parameters of the grating comprising the first 302 and second 303 layers (and perhaps also the thickness and scattering function parameters of the layers) and associated locations on the substrate may be stored in the database in connection with the identified substrate.

A determination 264 may be made as to whether there are more substrates to process in accordance with FIG. 2B. In other words, the procedure of FIG. 2B may be used to process, and make measurements upon, various individual substrates being manufactured.

The procedure 270 of FIG. 2C is similar to the procedure 250 of FIG. 2B, but takes the feed forward another step further. FIG. 2C also begins by re-identifying 272 the substrate to process.

Processing steps are performed 274 to form a feature or features on the identified substrate. For example, consider the configuration 370 of FIG. 3C which shows a substrate 101 after processing steps have been performed to form the grating with the three-layer (302, 303, and 304) mesa-like features.

Diffraction measurements may then be performed 276 at multiple locations on the identified substrate. Preferably, these multiple locations are the same ones as the multiple locations referred to in FIGS. 2A and 2B.

In addition, according to an embodiment of the present invention, previously-determined parameter data, along with associated locations, are retrieved 278 for this identified substrate from the database. For example, with reference to FIG. 3B, the shape parameters of the grating comprising the first 302 and second 303 layers (and perhaps also the thickness and scattering function parameters of the layers) and associated locations on the substrate may be retrieved from the database.

Subsequently, using the parameter data retrieved from the database, reduced-dimensionality computations may then be performed 280 to determine a value for at least one parameter at the multiple locations on the identified substrate. Advantageously, using the "feed forward" data from the previous processing step reduces the dimensionality (and, hence, reduce the complexity) of the scatterometry computation required for the current processing step. For example, with reference to FIG. 3C, the parameters of the three-layer mesa features may be determined with less variable parameters and hence with substantially less complexity by using the previously-determined parameters of the first two layers (302 and 303).

In accordance with an embodiment of the invention, the feed forward process may continue to further processing steps and scatterometry measurements. In such an embodiment, the parameter data and associated locations for the identified substrate, as determined in the preceding step 280, are then stored 282 in the database.

A determination 284 may be made as to whether there are more substrates to process in accordance with FIG. 2C. In other words, the procedure of FIG. 2C may be used to process, and make measurements upon, various individual substrates being manufactured.

Figure 4:
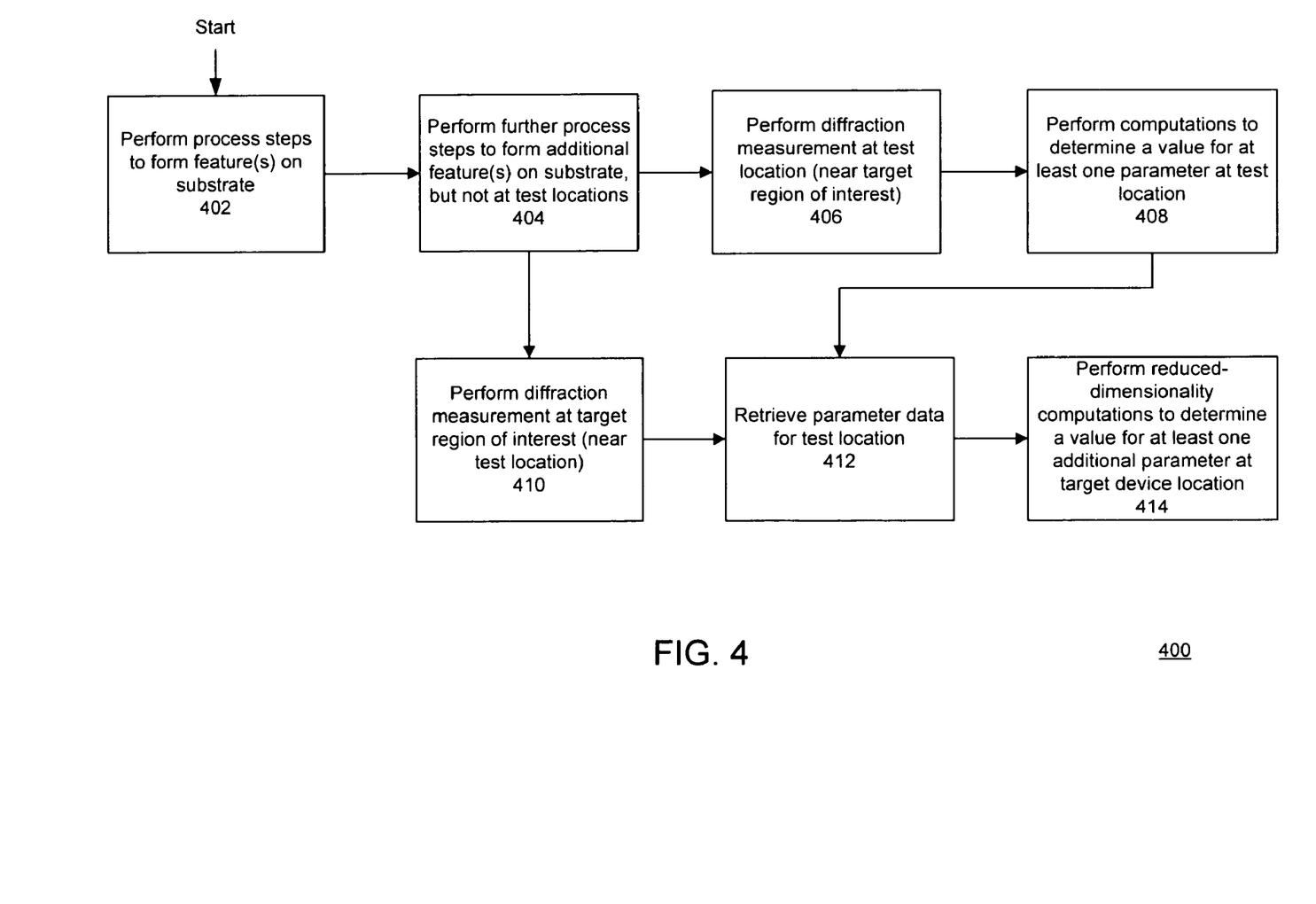
FIG. 4 is a flow chart depicting a method of model-based measurement of semiconductor device features using data from a test location for dimensionality reduction in accordance with an embodiment of the invention.
Figure 5:
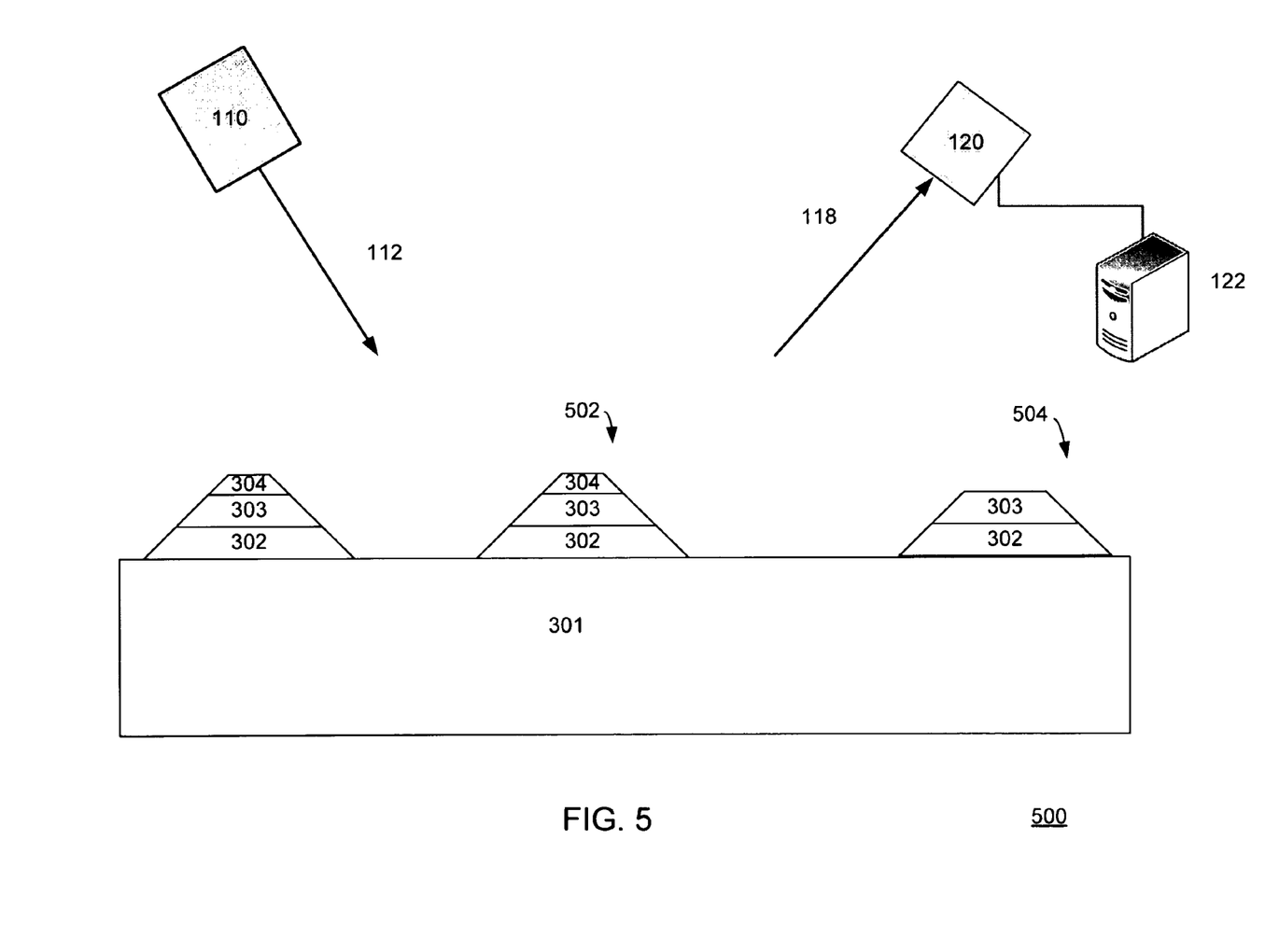
FIG. 5 is a schematic diagram depicting a scatterometry configuration applied to a semiconductor wafer with a device location and a test location in accordance with an embodiment of the invention.

FIG. 4 is a flow chart depicting a method 400 of model-based measurement of semiconductor device features using data from a test location for dimensionality reduction in accordance with an embodiment of the invention.

The method 400 of FIG. 4 begins with the performance 402 of processing steps to form a feature or features on the identified substrate. For example, consider the formation of the first 302 and second 303 layers of a grating pattern on the substrate 101 in the configuration 500 shown in FIG. 5.

Thereafter, further processing steps are performed 404 to form additional feature(s) on the substrate in the device regions, but not at test locations. For example, consider the formation of the third layer 304 of the grating pattern in the target region of interest 502, but not at the test location 504, as shown in FIG. 5

A diffraction measurement may then be performed 406 at a test location (preferably, near the target region of interest) on the identified substrate. For example, consider FIG. 5 which shows a diffraction measurement being performed on the two-layer grating pattern at the test location 504.

Using the diffraction measurement at the test location, computations are then performed to determine 408 a value for at least one parameter (such as, physical dimensions and electromagnetic scattering function parameters) of the feature(s) at the test location. These computations are the aforementioned model-based computations and may comprise, for example, library mode or real-time regression mode computations. For example, with reference to FIG. 5, the shape parameters (and perhaps the thicknesses and scattering function parameters) of the first 302 and second 303 layers at the test location 504 may be determined.

In addition, a diffraction measurement is performed 410 at a target region of interest (preferably, near the test location) on the identified substrate. For example, consider FIG. 5 which shows a diffraction measurement being performed on the triple-layer mesas in the target region of interest 502.

In addition, according to an embodiment of the present invention, previously-determined parameter data from a test location (preferably, in the near vicinity of the target region of interest) is retrieved 412 from the database. For example, with reference to FIG. 5, the shape parameters (and perhaps the thicknesses and scattering function parameters) of the first 302 and second 303 layers at the test location 504 on the substrate may be retrieved from the database.

Subsequently, using the parameter data retrieved from the database, reduced-dimensionality computations may then be performed 414 to determine a value for at least one additional parameter at the target region of interest. Advantageously, using the "feed forward" data from the test location reduces the dimensionality (and, hence, reduce the complexity) of the scatterometry computation required for the more complex feature(s) in the target region of interest. For example, with reference to FIG. 5, the parameters of the three-layer mesa features in the target region 502 may be determined with less variable parameters and hence with substantially less complexity by using the previously-determined parameters of the first 302 and second 303 layers from the test region 504.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of model-based measurement of semiconductor device features, the method comprising:
   identifying a substrate to process;
   performing process steps to form at least one feature on the identified substrate;
   performing measurements at multiple locations on the identified substrate;
   performing computations to determine at least one parameter at said multiple locations on the identified substrate;
   storing data for said at least one parameter, associated locations, and substrate identification in a database;
   re-identifying the substrate to process;
   performing process steps to form at least one additional feature on the identified substrate;
   performing measurements at said multiple locations on the identified substrate;
   retrieving said at least one parameter which was previously determined from the database; and
   using said at least one parameter determined prior to said re-identification to reduce a dimensionality required for real-time regression to determine at least one additional parameter at said multiple locations on the identified substrate.

2. The method of claim 1, wherein the measurements comprise optical diffraction measurements.

3. The method of claim 1, wherein said real-time regression requires less computing time than real-time regression with a larger number of variable parameters.

4. An apparatus for model-based measurement of semiconductor device features, the apparatus comprising:
   means for identifying a substrate to process;
   at least one processing tool for performing process steps to form at least one feature on the identified substrate;
   a measuring tool for performing measurements at multiple locations on the identified substrate;
   a data processing system for performing computations to determine at least one parameter at said multiple locations on the identified substrate;
   a data storage module for storing data for said at least one parameter, associated locations, and substrate identification in a database;
   a data retrieval module for retrieving said at least one parameter which was previously determined from the database,
   wherein the means for identifying is configured to subsequently re-identify the substrate to process,
   wherein the at least one processing tool is configured to subsequently perform process steps to form at least one additional feature on the identified substrate,
   wherein the measuring tool is configured to subsequently perform measurements at said multiple locations on the identified substrate, and
   wherein the computing system is configured to use said at least one parameter determined prior to said re-identification to reduce a dimensionality required for real-time regression to determine at least one additional parameter at said multiple locations on the identified substrate.

5. The apparatus of claim 4, wherein the measurements comprise diffraction measurements.

6. The apparatus of claim 5, wherein said real-time regression requires less computing time than real-time regression with a larger number of variable parameters.

7. A method of model-based measurement of semiconductor device features, the method comprising:
   performing process steps to form at least one feature on a substrate;
   performing process steps to form at least one additional feature on the substrate in a device region but not test locations;
   performing measurements at a test location;
   performing computations to determine at least one parameter at the test location;
   performing measurements at a target region of interest in the device region;
   retrieving said at least one parameter for the test location; and
   using said at least one parameter determined from the test location to reduce a dimensionality required for real-time regression to determine at least one additional parameter at said target region of interest.

8. The method of claim 7, wherein the test location is selected so as to be closely located to the target region of interest.

9. The method of claim 8, wherein the measurements comprise optical diffraction measurements.

10. The method of claim 9, wherein said reduced-dimensionality real-time regression requires less computing time than real-time regression with a larger number of variable parameters.

11. An apparatus for model-based measurement of semiconductor device features, the method comprising:

at least one processing tool for performing process steps to form at least one feature on a substrate and for performing process steps to form at least one additional feature on the substrate in a device region but not test locations;

a measuring system for performing measurements at a test location and for performing measurements at a target region of interest in the device region; and a computing system configured to perform computations to determine at least one parameter at the test location, to retrieve said at least one parameter for the test location, and to use said at least one parameter determined from the test location to reduce a dimensionality required for real-time regression to determine at least one additional parameter at said target region of interest.

12. The apparatus of claim 11, wherein the computing system is configured to select a test location so as to be closely located to the target region of interest.

13. The apparatus of claim 12, wherein the measurements comprise diffraction measurements.

14. The apparatus of claim 13, wherein said reduced-dimensionality real-time regression requires less computing time than real-time regression with a larger number of variable parameters.

* * * * *